(12) United States Patent
Mullins et al.

(10) Patent No.: US 11,297,852 B2
(45) Date of Patent: Apr. 12, 2022

(54) METHOD FOR TREATMENT OR PREVENTION OF GILL DISEASE

(71) Applicant: NUTRECO IP ASSETS B.V., Boxmeer (NL)

(72) Inventors: Julia Elizabeth Mullins, Ræge (NO); Charles McGurk, Brusand (NO); Øyvind Røn, Sandnes (NO)

(73) Assignee: NUTRECO IP ASSETS B.V., Boxmeer (NL)

( * ) Notice: Subject to any disclaimer, the term of this patent is extended or adjusted under 35 U.S.C. 154(b) by 0 days.

(21) Appl. No.: 16/437,635

(22) Filed: Jun. 11, 2019

(65) Prior Publication Data
US 2019/0320685 A1 Oct. 24, 2019

Related U.S. Application Data

(62) Division of application No. 15/752,449, filed as application No. PCT/NO2016/050164 on Aug. 1, 2016, now abandoned.

(30) Foreign Application Priority Data

Aug. 14, 2015 (NO) .................................. 20151028

(51) Int. Cl.
| | |
|---|---|
| *A23K 20/142* | (2016.01) |
| *A61K 31/198* | (2006.01) |
| *A23K 50/80* | (2016.01) |
| *A23K 20/174* | (2016.01) |
| *A23K 20/158* | (2016.01) |
| *A23K 40/25* | (2016.01) |
| *A23K 20/20* | (2016.01) |
| *A61P 33/04* | (2006.01) |
| *A23K 20/147* | (2016.01) |

(52) U.S. Cl.
CPC .......... *A23K 20/142* (2016.05); *A23K 20/158* (2016.05); *A23K 20/174* (2016.05); *A23K 20/20* (2016.05); *A23K 40/25* (2016.05); *A23K 50/80* (2016.05); *A61K 31/198* (2013.01); *A61P 33/04* (2018.01); *A23K 20/147* (2016.05); *A23K 20/30* (2016.05)

(58) Field of Classification Search
None
See application file for complete search history.

(56) References Cited

U.S. PATENT DOCUMENTS

2009/0162393 A1\* 6/2009 Cook .................. A61K 39/002
424/191.1
2011/0308474 A1 12/2011 Koppe et al.

FOREIGN PATENT DOCUMENTS

| | | |
|---|---|---|
| CN | 104814273 A | 8/2015 |
| EP | 1 234 508 A1 | 8/2002 |
| EP | 2 880 989 A1 | 6/2015 |
| WO | WO-2010/087715 A1 | 8/2010 |

OTHER PUBLICATIONS

Ascenzi, P., et al., 2003, "The ant-parasitic effects of nitric oxide", IUBMB Life, 55(10-11), s 573-578.
European Extended Search Report, dated Dec. 10, 2018, 10 pages.
Holen, E., et al., 2014, "A co culture approach show that polyamine turnover is affected . . . ", Fish Shellfish immunol, 37, s 286-298.
Krista Fischer-Stenger et al., The Arginine-Dependent Cytolytic Mechanism Plays a Role in Destruction of Naegleria Fowleri Amoebae by Activated Macrophages, Infection and Immunity, Dec. 1, 1992, Vo. 60, No. 12, pp. 5126-5131.
Mark D. Powell et al., Effect of Dietary Inclusion of N-Acetyl Cysteine on Mucus Viscosity and Susceptibility of Rainbow Trout, Oncorhynchus Mykiss, and Atlantic Salmon, Salmo Salar to Amoebic Gill Disease, Journal of The World Aquaculture Society, vol. 38, No. 3, Sep. 1, 2007, pp. 435-442.
Mitchell @ Rodger, 2011, "A review of infectious gill disease in marine salmonid fish ", Journ. of fish diseases, vol. 34, 6 s 411-432.
Mørkøre et al., 2010, "Optimalt fòr som gir fast filet", Nofima rapport 37/2010.
Nowak, Barbara et al., "Immunity to Amoeba"., Developmental and Comparative Immunology 43 (2014) 257-267.
Pennacchi, Y. et al., "Evidence of immune and inflammatory processes in the gills of AGD-affected Atlantic salmon, Salmo salar L.", Fish & Shellfish Immunology 36(2014) 563-570.
Pilsetskaya, E.M. et al., Abstract of "Effects of injected and dietary arginine on plasma insulin levels and growth of pacific salmon and rainbow trout", In: Comp. Biochem. Physiol. A Physiol., 1991, vol. 98, pp. 165-170.
Roberts, Shane D., "The viscosity and glycoprotein biochemistry of salmonid mucus varies with species, salinity and the presence of amoebic gill disease", J Comp Physiol B (2005) 175:1-11.
Svendsen, Njord, 2013, "Kosttilskot kan slanke laksen", En artikkel fra NIFES.
Zhenyan Cheng et al., Dietary Supplementation of Arginine and/or Glutamine Influences Growth Performance, Immune Responses and Intestinal Morphology of Hybrid Striped Bass (Morone Chrysops X Morone Saxatilis), Aquaculture, Jul. 20, 2012, vol. 362-363, pp. 39-43, Amsterdam, NL.
Anonymous, "Amoebozoa—Wikipedia", Jul. 9, 2019 (Jul. 9, 2019), XP055603836, Retrieved from the Internet: URL:https://en.wikipedla.org/wlki/Amoebozoa [retrieved on Jul. 9, 2019], 7 pages.

(Continued)

*Primary Examiner* — Robert T. Crow
*Assistant Examiner* — John P Nguyen
(74) *Attorney, Agent, or Firm* — Sunit Talapatra; Foley & Lardner LLP (57) ABSTRACT

Composition for treatment of mucus on fish gills for a therapeutic or a prophylactic treatment of an amoebic gill disease in fish, where the composition comprises an extruded fish feed supplemented with arginine; said fish feed comprising protein, binder, fat, vitamins and minerals; and a total arginine content of the fish feed is at least 3.0% (wt/wt) of a total feed weight.

12 Claims, 5 Drawing Sheets

(56) References Cited

OTHER PUBLICATIONS

Anonymous, "Neoparamoeba—Wikipedia", Jul. 9, 2019 (Jul. 9, 2019), XP055603848, Retrieved from the Internet: URL:https://en.wikipedia.org/wikl/Neoparamoeba [retrieved on Jul. 9, 2019], 1 page.

European Communication, Application No. 16 837 374.4, dated Jul. 15, 2019, 7 pages.

Andrew Roderick Bridle, Immune-Regulatory Genes in Amoebic Gill Disease: Potential for Immunomodulation, University of Tasmania, May 31, 2005, 195 pages.

Chinese Office Action and English Translation, Application No. 201680048190.1, dated Apr. 2, 2020, 12 pages.

Chinese Search Report and English Translation, Application No. 201680048190.1, dated Mar. 26, 2020, 3 pages.

Erika M. Plisetskaya et al., Effects of Injected and Dietary Arginine on Plasma Insulin Levels and Growth of Pacific Salmon and Rainbow Trout, Comp. Biochem. Physiol., vol. 98A, No. 1, 1991, pp. 165-170.

Gangfu Chen et al. Effect of Dietary Arginine on the Immune Response and Gene Expression in Head Kidney and Spleen Following Infection of Jian Carp with Aeromonas hydrophila, Fish & Shellfish Immunology, 44, 2015, pp. 195-202.

International Search Report, PCT/NO2016/050164, dated Oct. 28, 2016, 5 pages.

Norwegian Office Action, Application No. 20151028, dated Jan. 14, 2016, 3 pages.

Norwegian Search Report, Application No. 20151028, dated Jan. 14, 2016, 2 pages.

Norwegian Written Opinion, Application No. 20161256, dated Jan. 31, 2017, 3 pages.

Wang Liansheng et al., Research Advances in Arginine Nutrition of Fish, Journal of Northeast Agricultural University, Sep. 18, 2014, 7 pages.

Written Opinion, PCT/NO2016/050164, dated Oct. 28, 2016, 5 pages.

Y. Pennacchi et al., Evidence of Immune and Inflammatory Processes in the Gills of AGD-Affected Atlantic Salmon, Salmo salar L., Fish & Shellfish Immunology, 36, 2014, pp. 563-570.

Mitchell & Rodger, 2011, "A review of infectious gill disease in marine salmonid fish", Journ. of fish diseases, vol. 34, pp. 411-432.

European Search Report, Application No. 20 20 1092, dated Nov. 16, 2020, 3 pages.

Zhenyan Cheng et al., Dietary Supplementation of Arginine and/or Glutamine Influences Growth Performance, Immune Responses and Intestinal Morphology of Hybrid Striped Bass, vol. 362-363, Jul. 20, 2012, pp. 39-43.

\* cited by examiner

Figure 1 Survival in Atlantic salmon (*S. salar*) following challenge with *Paramoeba perurans* [Relative percent survival = (1 − (% mortality / % control mortality)) × 100]

Fig. 1

Figure 2 Survival in Atlantic salmon (*S. salar*) following challenge with *P. perurans*

Fig. 2

Figure 3: Survival in Atlantic salmon (S. salar) following challenge with P. perurans

Fig. 3

Figure 4: In vitro survival of Paramoeba pemaquidensis after 72 hours of incubation with mucus from fish fed Control 1' and Control 1' + A' diets.

Fig. 4

Figure 5: Viscosity of Atlantic salmon (*S. salar*) mucus at 80 rpm with standard deviation. The star denotes significant difference.

Fig. 5

Figure 6: Concentration of lysozyme in Atlantic salmon (*S. salar*) mucus with standard deviation. The star denotes significant difference.

Fig. 6

Figure 7: Concentration of polysaccharides in Atlantic salmon (*S. salar*) mucus with standard deviation. The star denotes significant difference.

Fig. 7

Figure 8: Concentration of lysozyme in Atlantic salmon (*S. salar*) mucus with standard deviation. The fish were fed control 2" and control 2" + A" diets.

Fig. 8

Figure 9: *In vitro* survival of *Paramoeba pemaquidensis* after 48 hours of incubation with mucus from fish fed Control 2" and Control 2" + A" diets with standard deviation. The star denotes significant difference.

Fig. 9

Figure 10: *In vitro* survival of *Paramoeba perurans* after 48 hours of incubation with mucus from fish fed Control 2" and Control 2" + A" diets with standard deviation. The star denotes significant difference.

Fig. 10

METHOD FOR TREATMENT OR PREVENTION OF GILL DISEASE

This application is a divisional application of U.S. application Ser. No. 15/752,449, filed Feb. 13, 2018, which is the National Stage of Application No. PCT/NO2016/050164 filed Aug. 1, 2016, which is based upon and claims the benefit of priority from Norway Application No. 20151028, filed Aug. 14, 2015, the entire contents of all of which are incorporated herein by reference.

The invention concerns a composition for treatment of mucus on fish gills. More particularly the invention concerns a composition for increasing the viscosity of the mucus on the fish gills. The invention also concerns a composition for increasing the content of a polysaccharide in the mucus. The treatment of the mucus is a therapeutic or prophylactic treatment of an amoebic gill disease in fish. The amoebic gill disease is caused by a marine amoeba and in particular the ameobic gill disease is caused by *Paramoeba perurans*. The fish may be a salmonoid fish such as an Atlantic salmon (*Salmo salar*) or a rainbow trout (*Onchorhynchus mykiss*).

Amoebic gill disease (AGD) is one of the most significant challenges facing the global marine salmonid farming industry. It is found in a variety of fish species both farmed and wild, including sea bream, turbot, ayu, mackerel and lump fish. It was reported in Australia in 1984 and since then has been found on the West coast of the US, in Ireland (1995), Scotland and Norway since 2006 and Chile (2007). Outbreaks generally occur late summer to early winter at water temperatures above 10° C., however, more recently it has been of concern year round.

AGD is caused by *Paramoeba perurans*, previously *Neoparamoeba perurans*, a free living and opportunistically parasitic amoeba, and can be fatal if left untreated. It has been estimated to account for up to 20% of total production costs in terms of treatments, decreased fish growth and fish mortality. *P. perurans* is a marine amoeba. *P. perurans* is an extracellular parasite belonging to the phylum Flabellinea.

Risk factors include high salinity, warmer water temperatures, high stocking density of fish, suspended organic matter in the water and earlier gill damage.

Clinically, AGD causes anorexia (decreased feed intake), respiratory distress, flared opercula and lethargy. Grossly, white to grey raised mucoid patches can be seen on the surface of the gills. The presence of the amoeba is often associated with excess mucus production in the gills. Microscopically, the disease is characterised by epithelial hyperplasia (increase in epithelial cell numbers) and lamellar fusion with mucous metaplasia. As the disease progresses inflammatory cells (neutrophils and macrophages) are recruited to oedematous regions in the lesions. Eosinophilic granular cells are sometimes seen in the blood vessels surrounding the filamental cartilage. Later on in the disease development, there is epithelial hypertrophy and epithelial stratification at the surface of the lesions with mucous cell recruitment, a decrease in chloride cell numbers and the formation of interlamellar vesicles which may contain amoebae.

Diagnosis is through microscopic examination of fresh gill mounts or of paraffin embedded fixed gill tissue and/or a specific PCR assay for *P. perurans*.

*Paramoeba pemaquidensis* was thought to be the causative agent of AGD before *P. perurans*. *P. pemaquidensis* is often found on the gills with *P. perurans* as part of a mixed infection. The behaviour of amoebae to adverse or toxic substances is believed to be similar only within the amoeba in the same family or group. Amoebae have a similar mechanism in which they curl up and retract their filopodia in an adverse environment.

Despite more than 30 years of research there are no vaccines or medicines licensed to treat AGD. Current treatment methods include bathing with either fresh water (2-3 hrs at <4 ppt salinity) or with a hydrogen peroxide bath (1000-1400 ppm $H_2O_2$ for 20 to 30 minutes). The hydrogen peroxide bath is typically not used above 15-16° C. and with caution at temperatures between 12/13° C.-15/16° C.

A variety of in feed and in bath chemical treatments have been tested to gain more effective removal of the amoebae from the gills. Oral supplementation with either levamisole or glucans had no significant impact on mortality levels. In a cohabitation trial oral administration of L-cysteine ethyl ester (LCEE) two weeks prior to challenge significantly delayed the progression of AGD associated gill pathology (Roberts S D, Powell M D. 2005. Oral L-cysteine ethyl ester (LCEE) reduces amoebic gill disease (AGD) in Atlantic salmon *Salmo salar*. Dis Aquat Org, 66(1):21-28). LCEE was found to reduce mucus viscosity in Atlantic salmon. Fresh water treatment is also thought to reduce the viscosity of the mucus by fracturing the mucus and helping it slough off the skin (Roberts S D. 2004. Improving the treatment of amoebic gill disease in salmonids with soft freshwater and the mucolytic drug L-cysteine ethyl ester. PhD thesis, University of Tasmania, Launceston.) Fresh water treatment and treatment with LCEE have in common a positive clinical effect on AGD, and they have in common that mucus viscosity is decreased.

Bithionol, an anti protozoal drug (no Maximum Residue Limit (MRL) established in any food animal species) used in feed at 25 mg/kg showed a delay and reduction in intensity of AGD associated lesions. Ionophores: Salinomycin, Lasalocid acid and Maduramycin used individually in in vitro bath treatments at 10 mg/l significantly reduced amoebae numbers. However, when tested as in feed treatments the ionophores only reduced the percent of lamella with lesions compared to the control fed fish at 7 days after *P. perurans* challenge. At 14 and 21 days after challenge there was no difference.

A thin layer of mucus is found upon fish gill and skin and is the first physical barrier of defence against water borne pathogens. Additionally, it has functions in respiration, ionic and osmotic regulation, reproduction, communication, excretion and disease resistance. The protective function of mucus is a combined result of mechanical and biochemical properties. The mucus is mainly secreted by mucous cells in the epidermis. In addition to trapping and sloughing of pathogens, mucus contains a wide range of substances which can have an effect on pathogens. Mucus is mainly composed of water and glycoproteins. However, a variety of components including a number of innate immune components such as lectins, pentraxines, lysozymes, proteolytic enzymes, alkaline phosphatase, C-reactive protein, complement and antimicrobial peptides as well as immunoglobulins have also been described in mucus.

More recently, changes in protein abundance in gill mucus have been described in salmon infected with *P. perurans*. This is supported by histological observations of gill lesions associated with AGD in that there is reduced attachment of amoebae to areas of epithelia with high numbers of mucous cells. The latter stages of AGD lesion development consist of squamation of superficial epithelia and variable recruitment of mucous cells to lesion surfaces which may be indicative of a fortification strategy designed to exclude and/or destroy or isolate the amoebae from susceptible tissue. Fusion of lamellae reduces the total surface area available for the amoebae to colonise. Enzymes and/or other substances secreted by the mucous cells may affect the recruitment and attachment of amoebae to these areas. (Adams M B, Ellard K, Nowak B F. 2004. Gross pathology and its relationship with histopathology of amoebic gill disease (AGD) in farmed Atlantic salmon, *Salmo salar* L. J Fish Dis, 27(3): 151-61; Adams M B, Nowak B F. 2003. Amoebic gill disease: sequential pathology in cultured Atlantic salmon, *Salmo salar* L. J Fish Dis, 26(10): 601-614.)

Patent document EP 1234508 discloses the use of L-arginine alone or in combination with ibuprofen for prophylactic treatment of coccidiosis in poultry. The causative organisms of coccidiosis are several species of *Eimeria*. *Eimeria* spp. are intracellular parasites belonging to the phylum Sporozoa or Apicomplexa. *Eimeria* spp. invade the epithelial cells lining the alimentary tract and the cells of associated glands.

The invention has for it's object to remedy or to reduce at least one of the drawbacks of the prior art, or at least provide a useful alternative to prior art.

The object is achieved through features, which are specified in the description below and in the claims that follow.

The invention is defined by the independent patent claim. The dependent claims define advantageous embodiments of the invention.

The results described below show that the addition of dietary arginine at levels above 3 percent total level in fish feed improved survival in AGD infected fish. This is important for the global marine salmon aquaculture in that an effective diet could help minimise AGD related costs through lower mortality rates, maintenance of growth rates and also perhaps less frequent bathing events.

In a first aspect the invention relates more particularly to a composition for treatment of mucus on fish gills for a therapeutic or a prophylactic treatment of an amoebic gill disease in fish, where the composition comprises an extruded fish feed supplemented with arginine; said fish feed comprising protein, binder, fat, vitamins and minerals; and a total arginine content of the fish feed is at least 3.0% (wt/wt) of a total feed weight.

The fish feed may be made by extrusion where the extruded mass is cooked and the extrudate is porous to absorb and keep a substantial amount of added liquid fat. The total amount of fat in the finished fish feed can be lower than 25%, it can be 25% and it can be higher than 25%, such as 30%, 35% and even 40% of the total weight of the fish feed. Starch from wheat and other vegetable raw materials such as faba beans, act as a binder to maintain shape and integrity of the fish feed. Other binders may also be used.

The treatment of the mucus may comprise an increase of a viscosity of the mucus. The treatment of the mucus may comprise an increase of a content of a polysaccharide in the mucus.

The amoebic gill disease may be caused by a marine amoeba. The fish may be a salmonoid fish such as Atlantic salmon or rainbow trout. The amoebic gill disease may be caused by an infection of at least one of the amoebae *Paramoeba perurans* syn. *Neoaramoeba perurans* and *Paramoeba pemaquidensis*, syn. *Neoparamoeba pemaquidensis*.

The fish feed may be for the prophylactic and/or therapeutic treatment of amoebic gill disease in fish. The fish feed may be for the prophylactic and/or therapeutic treatment of infections in fish by a marine amoeba. The fish feed may be for the prophylactic and/or therapeutic treatment of infections of at least one of the amoebae *Paramoeba perurans* syn. *Neoparamoeba perurans* and *Paramoeba pemaquidensis*, syn. *Neoparamoeba pemaquidensis*.

The onset of the prophylactic and/or therapeutic treatment may be by feeding the salmonoid fish the arginine supplemented feed 6 weeks after transfer of the salmonoid fish from fresh water to sea water. The fish feed may be for the prophylactic and/or therapeutic treatment of infections of at least one of the amoebae *Paramoeba perurans* syn. *Neoparamoeba perurans* and *Paramoeba pemaquidensis*, syn. *Neoparamoeba pemaquidensis*.

It is also described a use of arginine for treatment of mucus on fish gills for a therapeutic or a prophylactic treatment of an amoebic gill disease in fish. The arginine may be supplemented to fish feed in an amount sufficient to increase the total content of arginine in the fish feed to at least 3% (wt/wt) of the total feed weight.

The amoebic infection may be caused by at least one of the amoebas *Paramoeba perurans* syn. *Neoparamoeba perurans* and *Paramoeba pemaquidensis*, syn. *Neoparamoeba pemaquidensis*. The fish may be a salmonoid. Onset of feeding the fish feed to the fish according to the invention may be after transfer of the fish from fresh water to sea water. Onset of feeding the fish feed according to the invention to the fish may be 6 weeks after transfer of the fish from fresh water to sea water.

In the following are described examples of preferred embodiments.

EXAMPLE 1

The test was carried out with Atlantic salmon (*S. salar*) for 65 days in 250 l tanks containing salt water at 35 ppt salinity and at a water temperature of 16° C. There were 30 fish per tank with an average weight of 121 g at the start of the test and two tanks per diet.

The fish were acclimated and fed a control diet for five weeks prior to onset of the 65 day study period, then fed either the control diet or a test diet until trial end. The control diet, also termed control feed, Control 2, comprised wheat, wheat gluten, North Atlantic fish meal, soy protein concentrate, rapeseed oil, North Atlantic fish oil, astaxanthin, vitamins and minerals. The control diet was produced by extrusion cooking and was composed of 26.5% fat, 50.1% protein and 5.7% water and is representative of a commercial fish feed. The test diet, also termed test feed, Control 2+A, had the same composition as the Control 2 feed, but with arginine added at 1.0%. Arginine was added as a dry powder in the meal mix before cooking extrusion. The calculated total level of arginine in the Control 2 feed was 2.61% on an as is basis.

*P. perurans* were harvested from Atlantic salmon held in an infection tank following the methods described in Morrison R N, Crosbie P B B, Nowak B F. 2004. (The induction of laboratory-based amoebic gill disease revisited. J. Fish Dis, 27, 445-449). After four weeks of feeding the experimental diets, the fish were challenged with a total dose of 500 cells per litre of *P. perurans* over a series of days (0, 8, 9, 10, 12 and 16 post infection). For the challenge water circulation was stopped in all tanks and amoeba added to each tank using a watering can containing an additional 7 l of seawater to ensure even distribution of amoebae in the tank. Water flow was reinstated after 1.5-2 h.

The trial ended when the control group reached 60% mortality. The average fish weight at trial termination was 192 g. The presence of *P. perurans* in a selection of mortalities was confirmed by qPCR and histology.

Figure 1:
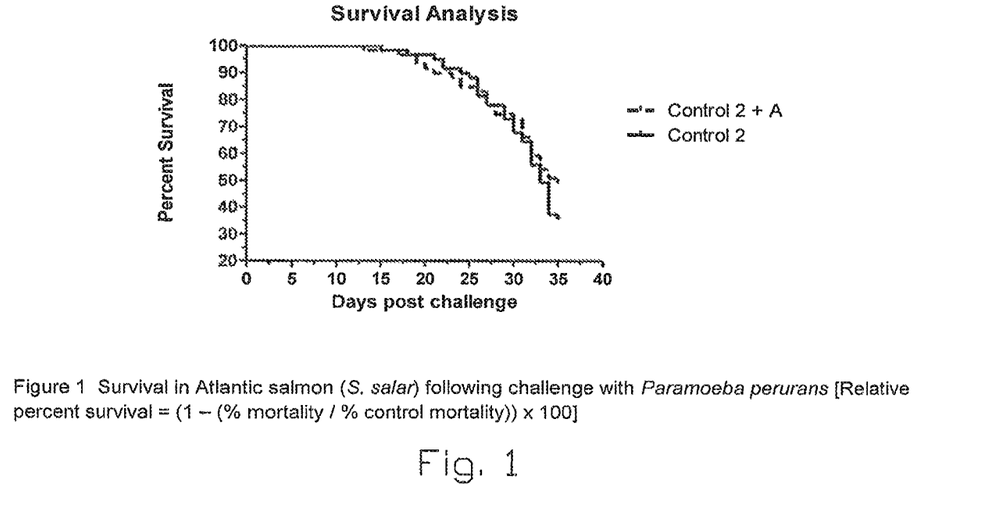
FIGS. 1-3 show survival in Atlantic salmon following challenge with the amoeba *Paramoeba perurans* in different studies.

As shown in FIG. 1, fish fed the test diet Control 2+A had a 19% relative percent survival compared to fish fed the control feed. Relative percent survival is calculated as: (1−(% mortality/% control mortality))×100.

Table 1 shows that the test diet was effective at reducing mortalities attributed to AGD compared to fish fed the control diet.

TABLE 1

Summary of mortalities at 35 days post infection

| Diet | Survival (%) | Mortality (%) |
| --- | --- | --- |
| Control 2 | 37 | 63 |
| Control 2 + A | 49 | 51 |

EXAMPLE 2

The test was carried out with Atlantic salmon (*S. salar*) for 144 days in 250 l tanks containing salt water at 35 ppt salinity and at a temperature of 16° C. There were 30 fish per tank with an average weight of 171 g at the start of the test and three tanks per diet.

The fish were acclimated and fed a control diet for four weeks, then fed either the control diet or test diet until trial end The control diet, also termed control feed, Control 1, comprised wheat, wheat gluten, sunflower meal, North Atlantic fish meal, soy protein concentrate, faba beans, rapeseed oil, North Atlantic fish oil, astaxanthin, vitamins and minerals. The control diet was produced by extrusion cooking and was composed of 24.2% fat, 49.9% protein 5.3% ash and 6.3% water and is representative of a commercial fish feed. The test diet, also termed test feed, Control 1+A, had the same composition as the Control 2 feed, but with arginine added at 0.58%. Arginine was added as a dry powder in the meal mix before cooking extrusion. Analysis showed that the Control 1 feed contained 2.92% arginine on an as is basis whereas the Control 1+A feed for the test group contained 3.24% arginine on an as is basis.

*P. perurans* were harvested from Atlantic salmon held in an infection tank following the methods described by Morrison et al. After four weeks of feeding the experimental diets, the fish were challenged with a total dose of 500 cells per litre of *P. perurans* over two days. Due to the low number of mortalities that were observed over the course of the challenge, an additional dose of amoebae (50 *P. perurans* cells/l) were also added on day 55 post challenge. For the challenge water circulation was stopped in all tanks and amoeba added to each tank using a watering can containing an additional 7 l of seawater to ensure even distribution of amoebae in the tank. Water flow was reinstated after 1.5-2 h.

The trial ended when the control group reached 40% mortality. The average fish weight at trial termination was 391 g. The presence of *P. perurans* in a selection of mortalities was confirmed by qPCR and histology.

Figure 2:
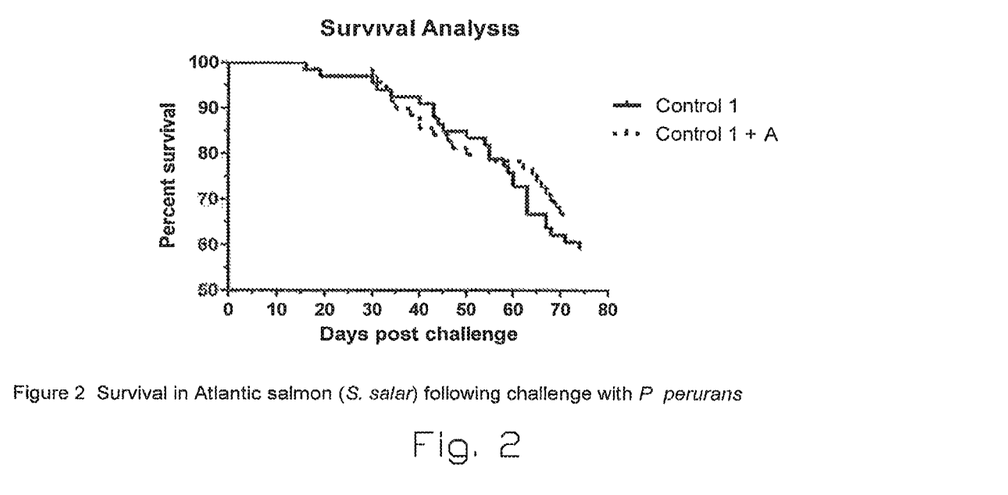

As shown in FIG. 2, fish fed the test diet, Control 1+A, had a 19% relative survival compared to fish fed the Control 1 feed.

Table 2 shows that the test diet was effective at reducing mortalities attributed to AGD compared to fish fed the control 1 diet.

TABLE 2

Summary of mortalities at 74 days post infection

| Diet | Survival (%) | Mortality (%) |
| --- | --- | --- |
| Control 1 | 59.1 | 40.9 |
| Control 1 + A | 66.7 | 33.3 |

EXAMPLE 3

The test was carried out with Atlantic salmon (*S. salar*) for 144 days in 250 l tanks containing salt water at 35 ppt salinity and at a temperature of 16° C. There were 30 fish per tank with an average weight of 179 g at the start of the test and three tanks per diet.

The fish were acclimated and fed a control diet for four weeks, then fed either the control diet or a test diet until trial end. The control diet, also termed control feed, Control 2', comprised wheat, wheat gluten, sunflower meal, North Atlantic fish meal, soy protein concentrate, faba beans, rapeseed oil, North Atlantic fish oil, astaxanthin, vitamins and minerals. The control diet was produced by extrusion cooking and was composed of 24.3% fat, 47.7% protein, 5.6% ash and 7.1% water and is representative of a commercial fish feed. The test diet, also termed test feed, Control 2'+A', had the same composition as the Control 2' feed, but with arginine added at 0.58%. Arginine was added as a dry powder in the meal mix before cooking extrusion. Analysis showed that the Control 2' feed contained 2.75% arginine on an as is basis whereas the Control 2'+A' feed for the test group contained 3.30% arginine on an as is basis.

*P. perurans* were harvested from Atlantic salmon held in an infection tank following the methods described by Morrison et al. After four weeks of feeding the experimental diets, the fish were challenged with a total dose of 500 cells per litre of *P. perurans* over two days. Due to the low number of mortalities that were observed over the course of the challenge, an additional dose of amoebae (50 *P. perurans* cells/l) were also added on day 55 post challenge. For the challenge water circulation was stopped in all tanks and amoeba added to each tank using a watering can containing an additional 7 l of seawater to ensure even distribution of amoebae in the tank. Water flow was reinstated after 1.5-2 h.

The trial ended when the control group reached 40% mortality. The average fish weight at trial termination was 422 g. The presence of *P. perurans* in a selection of mortalities was confirmed by qPCR and histology.

Figure 3:
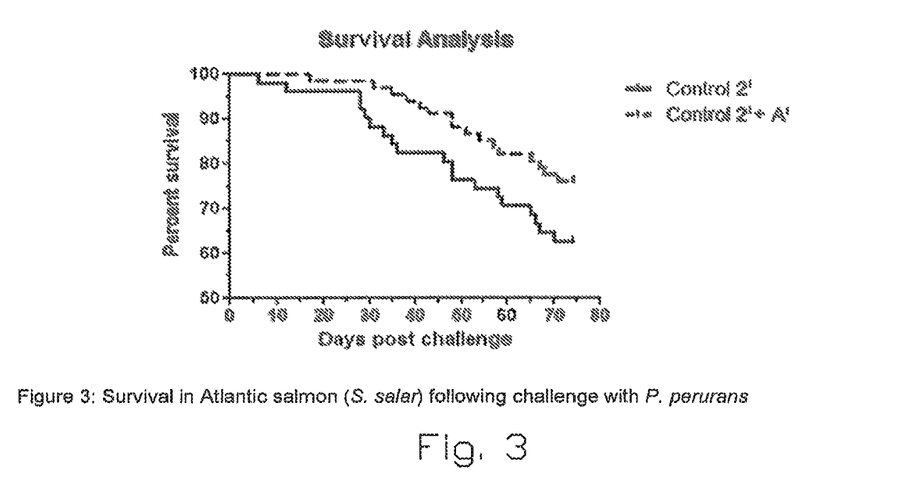

As shown in FIG. 3, fish fed the Control 2'+A' feed had a 36% relative survival compared to fish fed the Control 2' feed. Fish on the Control 2'+A' feed had a significantly increased survival compared to fish fed the Control 2 diet at the 0.1% level of significance (Log rank, Mantel-Cox, P=0.09).

Table 3 shows that the test diet was effective at reducing mortalities attributed to AGD compared to fish fed the Control 2' diet.

TABLE 3

Summary of mortalities at 74 days post infection

| Diet | Survival (%) | Mortality (%) |
|---|---|---|
| Control 2' | 62.7 | 37.3 |
| Control 2' + A' | 76.1 | 23.9 |

EXAMPLE 4

The test was carried out with Atlantic salmon (*S. salar*) for 37 days in tanks one meter in diameter containing salt water at 32.9-34.0 ppt salinity. Water temperature was varying from 11.8 to 12.1° C. There were 40 fish per tank with an average weight of 132 g at the start of the test and three tanks per diet.

The control diet, also termed control feed, Control 1', comprised wheat, wheat gluten, sunflower meal, Scandinavian fish meal, soy protein concentrate, rapeseed oil, North Atlantic fish oil, astaxanthin, vitamins and minerals. The control diet was produced by extrusion cooking and was composed of 23.2% fat, 48.0% protein, 11.1% ash and 4.9% water and is representative of a commercial fish feed. The test diet, also termed test feed, Control 1'+A', had the same composition as the Control 1' feed. Batches of 12.5 kg Control 1' feed was top coated with 1% arginine for 90 seconds in a commercial bread mixer before 0.05% Nordic fish oil was added and mixing continued for another 30 seconds.

At the end of the trial the fish weighed 156 g.

Protocol for Culturing Mucus Samples from Fish

Mucus Sampling:

Skin mucus was collected individually by placing each fish on a plastic bag, gently wrapping the bag around the fish and sliding the fish out of the bag. The mucus was immediately snap frozen in liquid nitrogen and stored at minus 80° C. until analysis. Skin mucus was taken instead of gill mucus because it was not possible to collect sufficient volume of gill mucus on individual fish for viscosity, lysozyme and polysaccharide analysis. Literature discloses that the skin and gill mucus are similar in characteristics for the analysed properties and changes in skin mucus reflect changes in gill mucus.

Mucus Preparation:

All mucus samples are thawed and used only once, re-use after refreezing is avoided as the activity of the substances or immunological components in the mucus may be influenced by freeze-thaw cycles. Depending on the viscosity of the mucus sample, the mucus sample is used as is. If the mucus sample is very viscous, the mucus sample is spin briefly for 1 min at 1000 g to settle the cells. The resulting supernatant is used for testing.

Incubation with Amoeba:

All mucus samples are diluted 1:1 with cultured amoebae of the species *Paramoeba pemaquidensis*. Amoebae are observed and checked for survival after 4-5 hours, 24 hours, 48 hours and after 6-9 days. A stronger effect in mucus is often observed after several days of exposure.

Vitality Staining:

The amoeba is stained by the fluorescent dyes propidium iodine, reddead cells, and fluorescein diacetate, green-live cells, for vitality staining, following a protocol by Yokoyama et al. (Journal of Fish Diseases 1997, 20 (4), 281-286) with a modified incubation time of only 5 minutes. As an alternative, the amoeba is stained by neutral red, which stains lysosomes in live cells (Chazotte, 2010, Imaging: A Laboratory Manual (ed. Yuste). CSHL Press, Cold Spring Harbor, N.Y., USA). Counts are performed in triplicate for 100 cells per concentration or per individual fish mucus sample.

Figure 4:
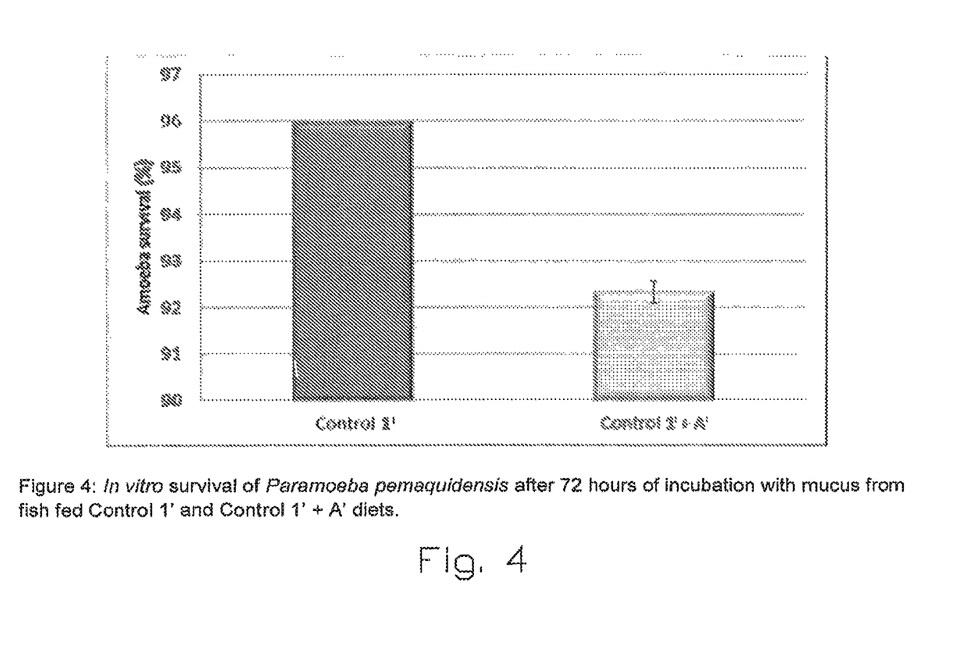
FIG. 4 shows in vitro survival of *Paramoeba pemaquidensis* after 72 hours of incubation with fish mucus.

Amoeba survival was decreased from 96 to 92 percent with 72 hours of incubation in mucus harvested from fish fed Control 1'+A' feed as shown in FIG. 4.

EXAMPLE 5

The test was carried out with Atlantic salmon (*S. salar*) for 34 days in tanks one meter in diameter containing salt water at 34.1-34.2 ppt salinity. Water temperature varied from 11.5 to 11.8° C. There were 20 fish per tank with an average weight of 379 g at the start of the test and one tank per diet.

The control diet, also termed control feed, Control 1", comprised wheat, wheat gluten, sunflower meal, North Atlantic fish meal, soy protein concentrate, faba beans, rapeseed oil, North Atlantic fish oil, astaxanthin, vitamins and minerals. The control diet was produced by extrusion cooking and was composed of 24.2% fat, 49.9% protein and 6.3% water and 5.3% ash and is representative of a commercial fish feed. The test diet, also termed test feed, Control 1"+A", had the same composition as the Control 1" feed, but with arginine added at 0.58%. Arginine was added as a dry powder in the meal mix before cooking extrusion. The analysed total level of arginine in the Control 1" feed was 2.92% on an as is basis and in the test diet Control 1"+A" it was 3.24% on an as is basis.

At the end of the trial the fish weighed on average 470.5 g. Skin mucus was collected individually by placing each fish on a plastic bag, gently wrapping the bag around the fish and sliding the fish out of the bag. The mucus was immediately snap frozen in liquid nitrogen and stored at minus 80° C. until analysis. Skin mucus was taken instead of gill mucus because it was not possible to collect sufficient volume of gill mucus on individual fish for viscosity, lysozyme and polysaccharide analysis. Literature discloses that the skin and gill mucus are similar in characteristics for the analysed properties and changes in skin mucus reflect changes in gill mucus.

Viscosity of the mucus was analysed on a Brookfield cone and plate DV3T rheometer. Mucus was centrifuged at 4000 rpm for four minutes and the viscosity of 0.5 ml of the clear particle free mucus was measured at 80 rpm at 12° C.

Lysozyme activity was measured on a Varioskan Flash plate reader. 250 µl of a suspension of *Micrococcus lysodeikticus* in 0.4 M sodium phosphate buffer at pH 5.8 was added to 5 µl of clear particle free mucus and the absorbance was followed for 30 minutes. A decrease in absorbance at 0.001 per minute was taken as a unit of lysozyme activity.

The amount of polysaccharide was measured on a Varioskan Flash plate reader. 25 µl of clear particle free mucus was mixed together with 60 µl of 2.5% phenol in water and 150 µl concentrated sulphuric acid, then incubated for 20 minutes at 100° C. After cooling to room temperature, the absorbance was measured and the concentration calculated based on standards containing glucose.

Figure 5:
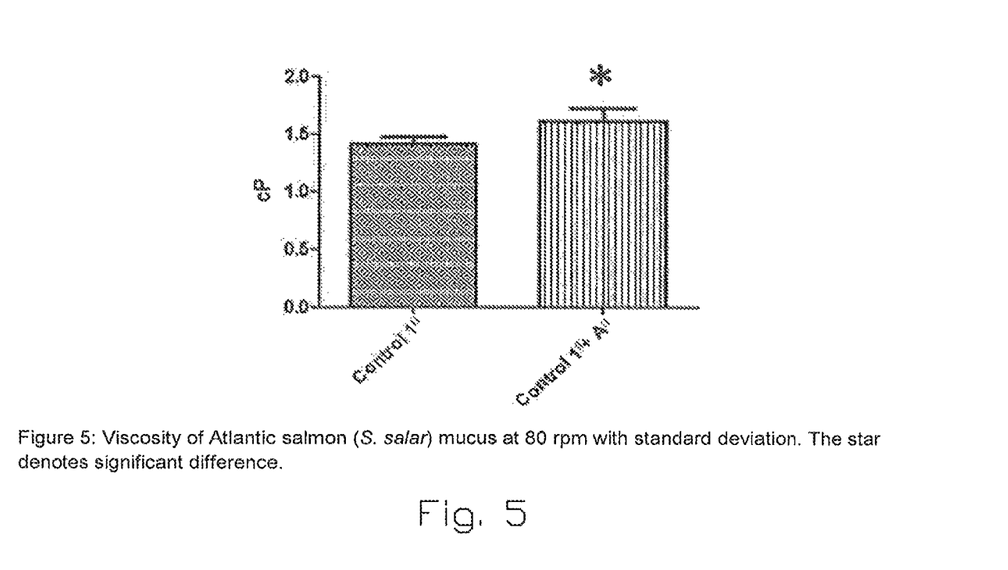
FIG. 5 shows viscosity of Atlantic salmon mucus.

FIG. 5 shows the viscosity of mucus at 80 revolutions per minute (rpm). The mucus was significantly thicker from fish in the test group fed Control 1"+A" feed than from fish in the control group fed Control 1" feed (P<0.0001, unpaired t test).

Figure 6:
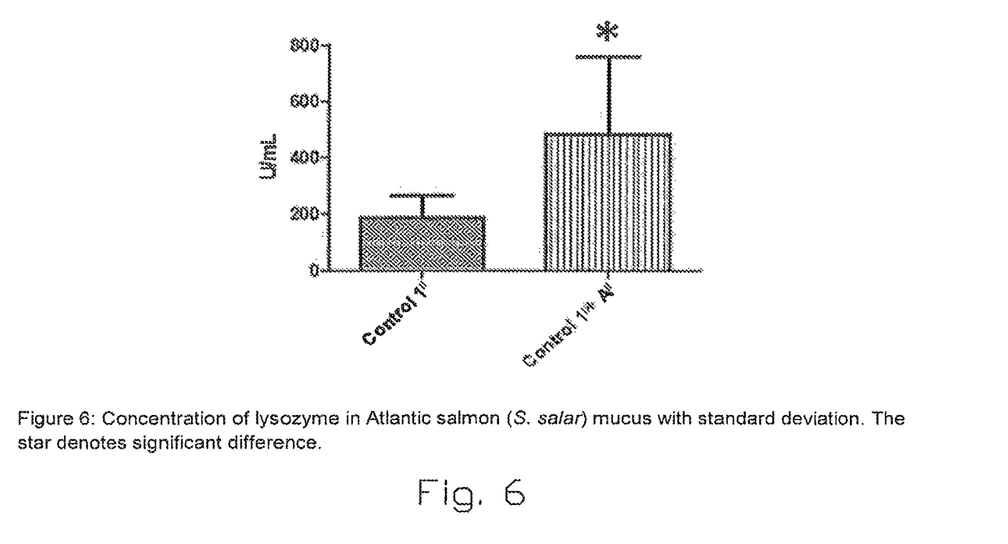
FIG. 6 shows concentration of lysozyme in Atlantic salmon mucus.
Figure 7:
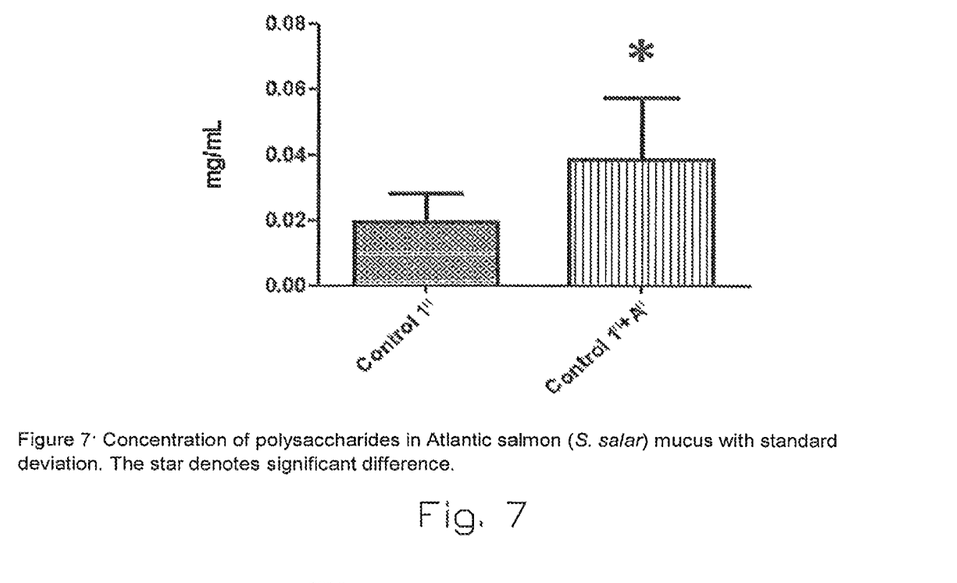
FIG. 7 shows concentration of polysaccharides in Atlantic salmon mucus.

Composition of the mucus from fish in the test group fed Control 1"+A" feed was significantly different from those in the control group fed Control 1" feed. The concentration of lysozyme in the mucus was significantly higher in the test group fed Control 1"+A" feed than in the control group fed Control 1" feed (P=0.0005, unpaired t test) as shown in FIG. 6. The concentration of polysaccharides was significantly higher in the test group fed Control 1"+A" feed (FIG. 7).

EXAMPLE 6

The test was carried out with Atlantic salmon (*S. salar*) for 41 days in tanks one meter in diameter containing salt water at 33.6-34.6 ppt. Water temperature ranged from 11.9° C. to 12.3° C. There were 30 fish per tank with an average weight of 322 g at the start of the test and two tanks per diet.

The control diet, also termed control feed, Control 2", comprised wheat, wheat gluten, North Atlantic fish meal, soy protein concentrate, faba beans, rapeseed oil, North Atlantic fish oil, sunflower meal, astaxanthin, vitamins and minerals. The control diet was produced by extrusion cooking and was composed of 25.8% fat, 45.0% protein, 7.3% water and 5.7% ash and is representative of a commercial fish feed. The test diet, also termed test feed, Control 2"+A", had the same composition as the Control 2" feed, but with arginine added at 0.86% as a dry powder in the meal mix before extrusion. The analysed total level of arginine in the Control 2" feed was 2.63% on an as is basis, in the test diet Control 2"+A" it was 3.14% on an as is basis.

At the end of the trial the fish weighed 545 g. Skin mucus was collected individually as described in example 4.

Figure 8:
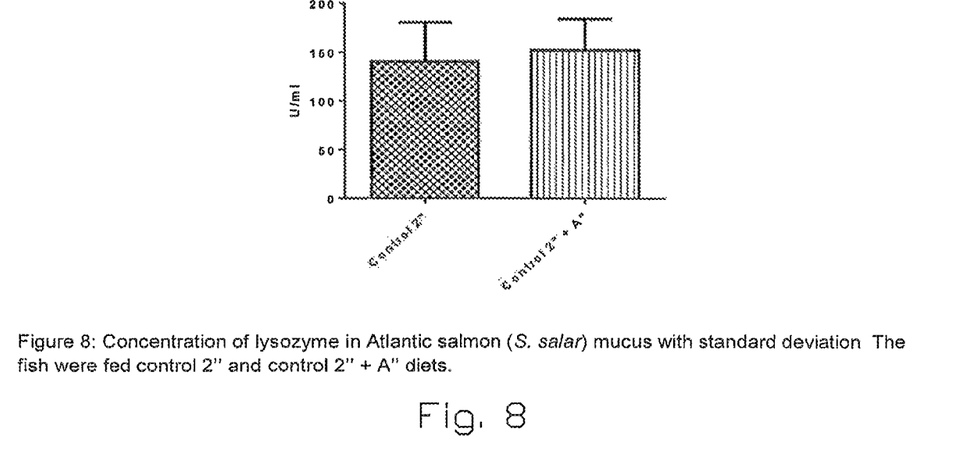
FIG. 8 shows concentration of lysozyme in Atlantic salmon mucus.

Lysozyme activity in the sampled mucus was measured as described in example 4. FIG. 8 shows the concentration of lysozyme in the mucus was higher in the test group fed Control 2"+A" than in the control group fed Control 2".

Incubation With Amoeba:

All mucus samples are diluted 1:1 with cultured amoebae either of the species *Paramoeba pemaquidensis* or of the species *Paramoeba perurans*. Amoebae are observed and checked for survival after 4-5 hours, 24 hours, 48 hours and 72 hours.

Figure 9:
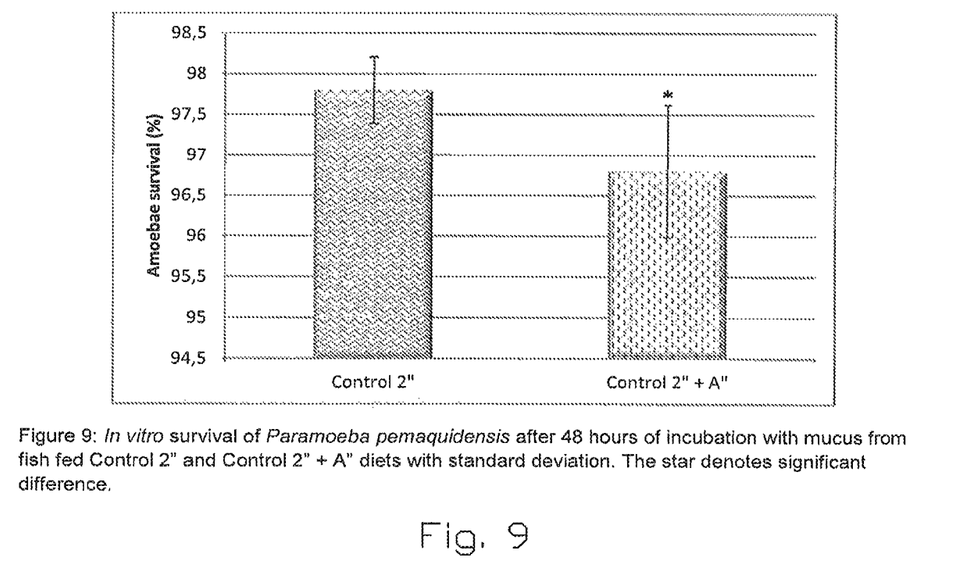
FIG. 9 shows in vitro survival of *Paramoeba pemaquidensis* after 48 hours of incubation with fish mucus.
Figure 10:
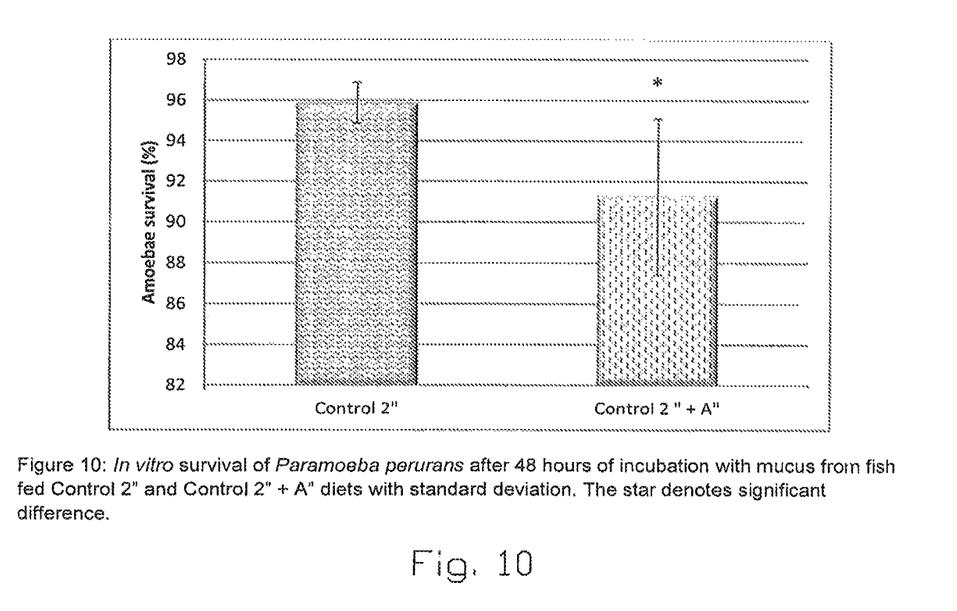
FIG. 10 shows in vitro survival of *Paramoeba perurans* after 48 hours of incubation with fish mucus.

Vitality staining was performed as described in example 4. *P. pemaquidensis* survival was significantly decreased from 97.8 to 96.8 percent (P=0.011, unpaired t test) after 48 hours of incubation and *P. perurans* survival was significantly decreased from 95.9 to 91.2 percent (P=0.004, unpaired t test) after 48 hours of incubation in mucus collected from fish fed Control 2"+A" feed as shown in FIGS. 9 and 10, respectively.

In addition, *P. pemaquidensis* survival was decreased from 96.6 to 91.8 percent after 72 hours of incubation and *P. perurans* survival was decreased from 92.1 to 90.2 percent 72 hours of incubation in mucus collected from fish fed Control 2"+A" feed.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements.

The mere fact that certain measures are recited in mutually different dependent claims does not indicate that a combination of these measures cannot be used to advantage.

The invention claimed is:

1. A method of increasing a mucus viscosity of a fish in need thereof, comprising determining that the fish is in need of increased mucus viscosity, and providing an extruded fish feed to the fish in need thereof, wherein the extruded fish feed comprises a total arginine content of at least 3.0% (wt/wt) of total feed weight.

2. The method of claim 1, wherein the extruded fish feed comprises protein, binder, fat, vitamins, and minerals.

3. The method of claim 1, wherein the fish comprises a salmonid fish.

4. The method of claim 3, wherein the salmonid fish comprises at least one of rainbow trout or Atlantic salmon.

5. A method of increasing a polysaccharide concentration in the mucus of a fish in need thereof, comprising determining that the fish is in need of increased polysaccharide concentration in the mucus, and providing an extruded fish feed to the fish in need thereof, wherein the extruded fish feed comprises a total arginine content of at least 3.0% (wt/wt) of total feed weight.

6. The method of claim 5, wherein the extruded fish feed comprises protein, binder, fat, vitamins, and minerals.

7. The method of claim 5, wherein the fish comprises a salmonid fish.

8. The method of claim 7, wherein the salmonid fish comprises at least rainbow trout or Atlantic salmon.

9. A method of increasing a lysozyme concentration in the mucus of a fish in need thereof, comprising determining that the fish is in need of increased lysozyme concentration in the mucus, and providing an extruded fish feed to the fish in need thereof, wherein the extruded fish feed comprises a total arginine content of at least 3.0% (wt/wt) of total feed weight.

10. The method of claim 9, wherein the extruded fish feed comprises protein, binder, fat, vitamins, and minerals.

11. The method of claim 9, wherein the fish comprises a salmonid fish.

12. The method of claim 11, wherein the salmonid fish comprises at least rainbow trout or Atlantic salmon.

* * * * *